United States Patent [19]

Cotting et al.

[11] Patent Number: 4,857,607
[45] Date of Patent: Aug. 15, 1989

[54] EPOXIDIZED POLYCYCLOACETALS

[75] Inventors: Jacques-Alain Cotting, Düdingen; Alfred Renner, Muntelier, both of Switzerland

[73] Assignee: Ciba-Geigy Corporation, Hawthorne, N.Y.

[21] Appl. No.: 195,312

[22] Filed: May 18, 1988

[30] Foreign Application Priority Data

May 27, 1987 [CH] Switzerland .......................... 2050/87

[51] Int. Cl.$^4$ ............................................. C08G 59/24
[52] U.S. Cl. .................................. 525/471; 525/472; 528/222; 528/232; 528/403; 528/418
[58] Field of Search ................ 525/471, 472; 528/222, 528/232, 418, 403; 549/334, 335

[56] References Cited

U.S. PATENT DOCUMENTS

| | | |
|---|---|---|
| 2,963,464 | 12/1960 | Cohen et al. |
| 3,041,313 | 6/1962 | Lavin ................................. 525/472 |
| 3,061,566 | 10/1962 | Kass et al. |
| 3,884,944 | 5/1975 | Renner et al. |
| 4,081,459 | 3/1978 | Mathais ............................. 528/418 |
| 4,374,953 | 2/1983 | Chou et al. ......................... 525/153 |
| 4,549,008 | 10/1985 | Renner et al. |

*Primary Examiner*—Harold D. Anderson
*Assistant Examiner*—T. Mason
*Attorney, Agent, or Firm*—Stephen V. O'Brien

[57] ABSTRACT

The invention relates to polycycloacetals of formula I

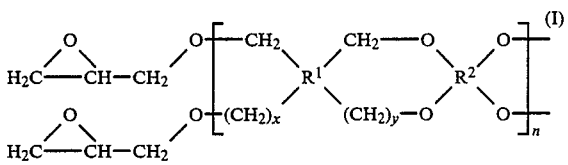
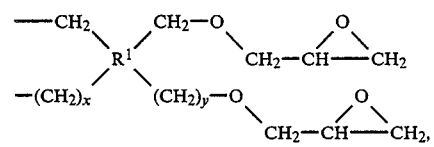

wherein n is an integer from 1 to 500, x and y are each independently of the other 0 or 1, $R^1$ is a carbon atom or a tetravalent hydrocarbon radical having a molecular weight not greater than 1000 and which can additionally contain ether oxygen atoms or oxygen atoms in hydroxyl, carbonyl or epoxy groups, and $R^2$ is a tetravalent hydrocarbon radical derived from a dialdehyde or a diketone.

The polycycloacetals can be used together with conventional hardeners and/or curing catalysts for epoxy resins for the fabrication of cross-linked (cured) products having good properties, especially having excellent fastness to solvents, light and weathering.

14 Claims, No Drawings

EPOXIDIZED POLYCYCLOACETALS

The present invention relates to epoxidised polycycloacetals, to a process for their preparation and to the use thereof for the fabrication of crosslinked cured products.

Epoxy resins find utility in numerous fields, for example as adhesives, varnishes, moulding compositions, insulating materials and composites, and a very wide range of chemically different epoxy resins are commercially available. The commonly employed epoxy resins are glycidyl derivatives of a bisphenol, a dicarboxylic acid or a diamine and epichlorohydrin. Polyglycidyl ethers of aliphatic and cycloaliphatic polyols are also used for specific utilities, which ethers have a relatively low viscosity compared with the aromatic systems referred to above and are therefore suitable, for example, for solvent-free coatings.

Epoxidised cyclic acetals are known in the art. Thus U.S. Pat. No. 3,884,944 discloses acetals which are derived from 2-epoxypropoxypivaldehyde and in which, for example, ethylene glycol, glycerol, pentaerythritol, 2,2,6,6-tetramethylolcyclohexanol or 2,2,6,6-tetramethylolcyclohexanone is used as diol or polyol component. Tetraglycidyl ethers of tetramethylolcycloalkanols and tetramethylolcycloalkanones, for example 2,2,6,6-tetramethylolcyclohexanol tetraglycidyl ether, are disclosed in U.S. Pat. No. 4,549,008.

Specifically, the present invention relates to epoxidised polycycloacetals of formula I

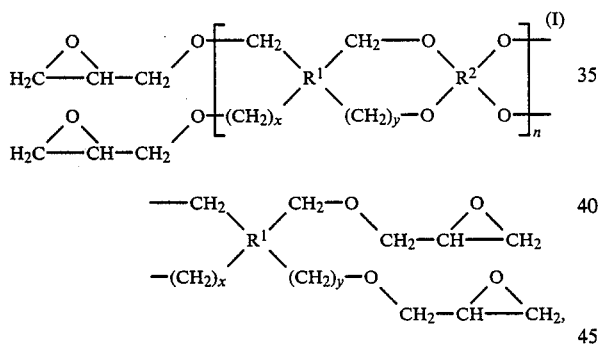

wherein n is an integer from 1 to 500, x and y are each independently of the other 0 or 1, $R^1$ is a carbon atom or a tetravalent hydrocarbon radical having a molecular weight not greater than 1000 and which can additionally contain ether oxygen atoms or oxygen atoms in hydroxyl, carbonyl or epoxy groups, and $R^2$ is a tetravalent hydrocarbon radical derived from a dialdehyde or a diketone.

The polycycloacetals of this invention are suitable epoxy resins for the fabrication of crosslinked products.

Accordingly, the invention also relates to curable mixtures comprising
(a) an epoxidised polycycloacetal of formula I, and
(b) a hardener and/or a curing catalyst for epoxy resins.

Preferred polycycloacetals of formula I are those wherein x and y are 1, as well as polycycloacetals of formula I, wherein one of the symbols x and y is 1 and the other is 0.

Further preferred polycycloacetals of formula I are those wherein n is an integer from 1 to 50, preferably from 2 to 20.

$R^1$ in formula I is preferably a carbon atom or a tetravalent $C_2$-$C_{24}$aliphatic, $C_5$-$C_{24}$cycloaliphatic or $C_6$-$C_{24}$aromatic radical. The aliphatic and cycloaliphatic radicals can contain keto groups, can be substituted by hydroxyl or glycidoxy groups or also be interrupted in the chain by ether oxygen atoms. The aliphatic radicals can be straight chain or branched. The cycloaliphatic radicals can contain one or more rings or they can be bicyclic or polycyclic systems. The aromatic radicals can contain one or more rings or fused rings and also comprise tetravalent radicals of formula

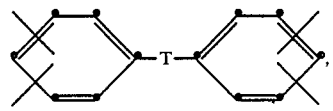

wherein T is methylene, isopropylidene, O, CO, S, SO or $SO_2$.

Particularly preferred polycycloacetals of formula I are those wherein $R^1$ is a carbon atom or a tetravalent $C_2$-$C_{12}$aliphatic, $C_5$-$C_{12}$cycloaliphatic radical or a $C_6$-$C_{12}$aromatic radical.

Most preferably, $R^1$ is a carbon atom or a group of formula

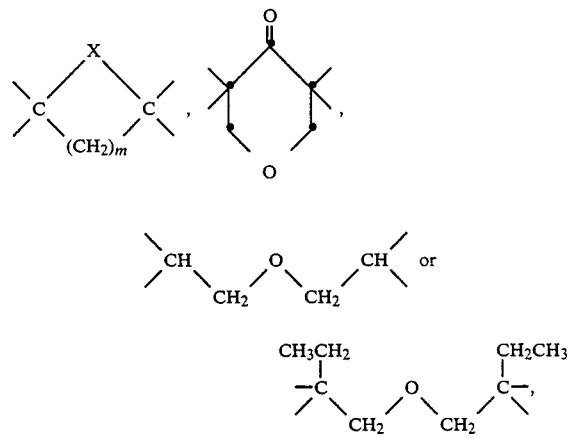

wherein X is a group selected from

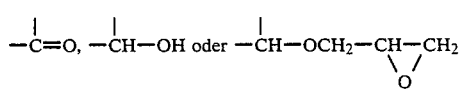

and m is an integer from 2 to 5.

$R^1$ preferably has a molecular weight of not more than 500, in particular of not more than 250 and, most preferably, of not more than 150.

The radical $R^2$ of the polycycloacetals of this invention is preferably a tetravalent $C_2$-$C_{12}$aliphatic radical, $C_5$-$C_{12}$cycloaliphatic radical or $C_6$-$C_{12}$aromatic radical. What has been discussed in connection with the radicals $R^1$ also applies to the aliphatic, cycloaliphatic and aromatic radicals $R^2$.

Particularly preferred polycycloacetals are those wherein $R^2$ is a group of formula

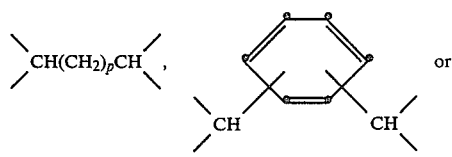

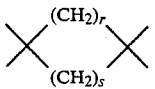

wherein p is 0 or an integer from 1 to 10 and r and s are each independently of the other an integer from 1 to 5 and the sum of r+s is $\leq 6$.

Most preferably, $R^2$ is a group of formula

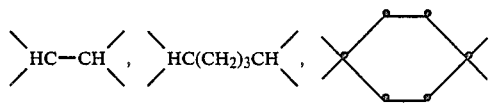

The most preferred polycycloacetals are those wherein $R^2$ is

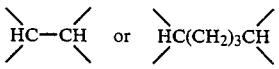

and $R^1$, where x and y are 1, is

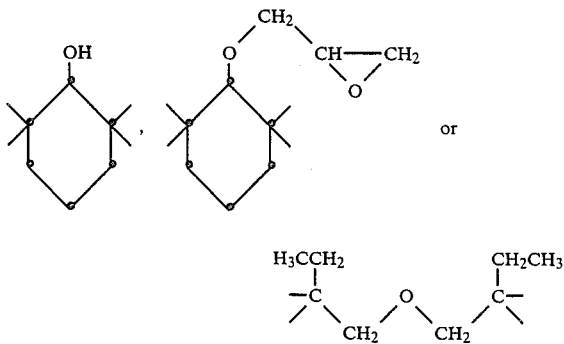

and where x or y is 0 and y or x is 1, is

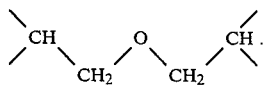

The polycycloacetals of this invention can be obtained, for example, by reacting a polyol of formula II

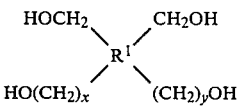

with a dialdehyde or a diketone to give a hydroxylated polycycloacetal of formula III

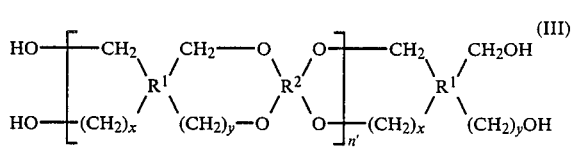

and subsequently glycidylating the compound of formula III with epichlorohydrin, in which formulae (II) and (III) above x, y, $R^1$ and $R^2$ have the given meanings and n' is an integer from 1 to 500.

Hydroxylated polycycloacetals are known in the art and can be prepared in known manner. Thus U.S. Pat. No. 2,963,464 discloses thermoplastic, high melting polycycloacetals which are prepared, for example, from pentaerythritol and a dialdehyde such as glutaraldehyde, or from diketones such as 2,4-pentanedione. Similar hydroxylated polycycloacetals and the preparation thereof are also disclosed in German Offenlegungsschrift 1 247 655 and U.S. Pat. No. 4,374,953.

Polyols of formula III which are especially suitable for the preparation of the epoxidised polycycloacetals of this invention are, for example, pentaerythritol, 2,2,6,6-tetramethylolcyclohexanol, 2,2,6,6-tetramethylolcyclohexanone, 2,2,6,6-tetramethyl-4-oxacyclohexanone, bis(2,3-dihydroxypropyl) ether (diglycerol), and bis(trimethylol)propane. Polyols of formula III are known and some are commercially available. Tetramethylolcycloalkanols and tetramethylolcycloalkanones can be prepared, for example, by the process disclosed in U.S. Pat. No. 2,462,031. Bis(trimethylol)propane und diglycerol can be prepared, for example, by condensation of trimethylolpropane or glycerol. These compounds are also commercially available (for example from Perstorp AG, Perstorp, Sweden or Tokyo Kasei, Japan). Particularly suitable dialdehydes or diketones are, for example, glyoxal, glutaraldehyde, succinaldehyde, terephthalaldehyde, isophthaldehyde and 1,4-cyclohexanedione.

The polycondensation of the polyol of formula II with the dialdehyde or diketone to give the hydroxylated polycycloacetal of formula III is preferably carried out in an inert organic solvent such as toluene with an acid catalyst, for example in the presence of $H_3PO_2$, and with simultaneous removal of water from the reaction mixture, preferably by azeotropic distillation.

The glycidylation of the hydroxylated polycyloacetals of formula III to give the epoxidised polycycloacetals of formula I is carried out in a manner known per se by reaction with epichlorohydrin in the presence of a base such as aqueous sodium hydroxide. Especially good results are obtained by reacting the hydroxylated polycycloacetals of formula III with epichlorohydrin in the presence of a phase transfer catalyst, followed by dehydrochlorination of the condensate with a base such as aqueous sodium hydroxide. Examples of suitable phase transfer catalysts are tertiary sulfonium salts, quaternary phosphonium salts and, preferably, quaternary ammonium salts. It is preferred to use, for example, tetraethylammonium salts, tetrabutylammonium salts, benzyltrimethylammonium salts and, in particular, tetramethylammonium salts, for example chlorides. It is preferred to carry out the reaction with an excess of epichlorohydrin without a solvent, the phase transfer catalyst and the base being added as aqueous solutions. During the reaction the solvent water and the water of reaction can conveniently be removed continuously by azeotropic distillation. It is, however, also possible to effect addition of an amount of epichlorohydrin equivalent to the OH groups in the presence of a catalytic amount of a Lewis acid ($SnCl_4$, $BF_4$ and the like) and to dehydrochlorinate the poly-2-hydroxy-3-chloropropyl ether with aqueous sodium hydroxide (q.v. U.S. Pat. No. 4,549,008, Example 1).

As already mentioned, the polycycloacetals of formula I are suitable for use as epoxy resins for the fabrication of crosslinked products.

Typical examples of hardeners are the conventional hardeners for epoxy resins, including aliphatic, cycloaliphatic, aromatic and heterocyclic amines such as bis(4-aminophenyl)methane, aniline/ formaldehyde resin, bis(4-aminophenyl)sulfone, propane-1,3-diamine, hexamethylenediamine, diethylenetriamine, triethylenetetramine, 2,2,4-trimethylhexane-1,6-diamine, m-xylylenediamine, bis(4-aminocyclohexyl)methane, 2,2-bis(4-aminocyclohexyl)propane and 3-aminomethyl-3,5,5-trimethylcyclohexylamine (isophoronediamine); polyaminoamides such as those obtained from aliphatic polyamines and dimerised or trimerised fatty acids; polyphenols such as resorcinol, hydroquinone, 2,2-bis(4-hydroxyphenyl)propane and phenol/aldehyde resins; polythiols such as the polythiols commercially available as "thiokols"; polycarboxylic acids and anhydrides thereof, for example phthalic anhydride, tetrahydrophthalic anhydride, hexahydrophthalic anhydride, hexachloroendomethylenetetrahydrophthalic anhydride, pyromellitic anhydride, 3,3',4,4'-benzophenonetetracarboxylic dianhydride, the acids of the aforementioned anhydrides as well as isophthalic acid and terephthalic acid. Suitable hardeners are also carboxyl-terminated polyesters, especially if the curable mixtures of this invention are used as powder coating compositions for surface protection. It is also possible to use catalytic hardeners, for example tin salts of alkanoic acids, e.g. tin octanoate, Friedels-Craft catalysts such as boron trifluoride and boron trichloride and their complexes and chelates which are obtained by reacting boron trifluoride with e.g. 1,3-diketones.

The amount of hardener employed depends on the chemical nature of the hardener and on the desired properties of the curable mixture and of the cured product. The maximum amount can be easily determined. If the hardener is an amine, 0.75 to 1.25 equivalents of active hydrogen bound to amino nitrogen per epoxide equivalent are normally used. If the hardener is a polycarboxylic acid or an anhydride thereof, then usually 0.4 to 1.1 equivalents of carboxyl group or anhydride group are used per equivalent of epoxy group. If the hardener is a polyphenol, it is convenient to use 0.75 to 1.25 phenolic hydroxyl groups per epoxide equivalent.

Catalytic hardeners are generally used in amounts of 1 to 40 parts by weight per 100 parts by weight of epoxy resin.

Curing accelerators may also be used for the curing. Examples of such curing accelerators are: tertiary amines, the salts or quaternary ammonium compounds thereof, e.g. benzyldimethylamine, 2,4,6-tris(dimethylaminomethyl)phenol, 1-methylimidazole, 2-ethyl-4-methylimidazole, 4-aminopyridine, tripentylammonium phenolate, or alkali metal alcoholates such as sodium alcoholates of 2,4-dihydroxy-3-hydroxymethylpentane. Curing of the mixtures of the invention is conveniently carried out in the temperature range from 15° to 300° C., preferably from 25° to 250° C.

Curing can be carried out in known manner in two or more steps, the first curing step being effected at low temperature and the post-curing at more elevated temperature.

If desired, curing can be carried out in two steps such that the curing reaction is first prematurely discontinued or the first step is carried out at slightly elevated temperature to give a still fusible and/or soluble curable precondensate (B-stage) from the epoxy component (a) and the hardener (b). Such a precondensate can be used, for example, as varnish component and, if desired, for the preparation of prepregs.

The term "curing" as employed herein means the conversion of the soluble, either liquid or fusible polyepoxide into solid, insoluble and infusible three-dimensional crosslinked products or moulding materials, normally accompanied by simultaneous shaping to moulded articles such as castings, mouldings and laminated materials, and to impregnations, coatings, films or bonds.

The curable mixtures of this invention further contain suitable plasticisers such as dibutyl phthalate, dioctyl phthalate or tricresyl phthalate.

Finally, the curable mixtures can be blended, before curing, in any phase with diluent, fillers and reinforcing agents, for example coal-tar, bitumen, textile fibres, glass fibres, asbestos fibres, boron fibres, carbon fibres, mineral silicates, mica, powdered quartz, alumina trihydrate, bentonites, kaolin, silica aerogel or metal powders, for example aluminium powder or iron powder, and also pigments and dyes, such as carbon black, oxide colourant, titanium dioxide and the like. It is also possible to add other customary additives, for example flame retardants such as antimony trioxide, thixotropic agents or flow control agents such as silicones, waxes or stearates (some of which can also be used as mould release agents), to the curable mixtures.

The preparation of the curable mixtures of this invention can be effected in conventional manner using known mixing units (stirrers, kneaders, rolls etc).

The curable epoxy resin mixtures of this invention are used, in particular, in the fields of surface protection, electrical engineering, laminating and construction. They can be used in a formulation adapted to suit each particular end use, in an unfilled or filled state, as paints, varnishes, such as sintered powder coating competitions, as compression moulding materials, dipping resins, casting resins, injection moulding formulations, impregnating resins and adhesives, tool resins, laminating resins, sealing and patching compounds, flooring materials and binders for mineral aggregates.

The compounds of this invention are especially suitable for utilities in surface protection, for example in the electrocoating of metals, as components of varnishes and paints and, in addition, of adhesives and electrical insulating materials.

Depending on the structure of the polycycloacetals of formula I, the compositions of this invention can be used for obtaining solvent-free liquid epoxy resin coatings, as components of solvent-containing varnishes or also of powder coating compositions.

The cured products obtained with the compounds of formula I are distinguished by good chemical, thermal and mechanical properties, especially by excellent fastness to solvents, light and atmospheric influences.

The invention is illustrated in more detail by the following Examples.

EXAMPLE 1

Polycondensate of 2,2,6,6-tetramethylolcyclohexanol and glutaraldehyde, etherified with epichlorohydrin

Part A: Preparation of the hydroxylated polycycloacetal 90 parts of 2,2,6,6-tetramethylolcyclohexanol and 0.3 part of hypophosphorous acid are suspended at 85° C. in 500 parts of toluene. Then 68 parts of a 50% aqueous solution of glutaraldehyde are added dropwise to the suspension over 30 minutes. Distillation of water through a water separator is commenced by lowering the pressure to ca. 0.15 bar. When the water separation is complete, the reaction mixture is heated under reflux for a further 2 hours under a pressure of 1 bar. The reaction mixture is then cooled to 30° C., the toluene phase is decanted, the product is dissolved in 350 parts of methanol, and the methanol is removed by distillation in a rotary evaporator. The residue is dried at 120° C./0.02 bar.

Yield: 119 parts (97% of theory)
Softening point: 131° C.
$\overline{M}n$ (gel permeation chromatography in THF)=1247, $\overline{M}w/\overline{M}n$=2.078
Hydroxyl content: 7.29 eq./kg.

Part B: Preparation of the epoxidised polycycloacetal 100 parts of the polycycloacetal obtained in A and 2 parts of a 50% aqueous solution of tetramethylammonium chloride are dissolved at 60° C. in 337 parts of epichlorohydrin. Distillation of epichlorohydrin through a water separator is initiated by lowering the pressure to ca. 0.15 bar. Then 64 parts of a 50% aqueous solution of sodium hydroxide are added dropwise over 1 hour, while simultaneously removing water continuously by distillation. When the water separation is complete, distillation is continued for 5 hours while returning epichlorohydrin to the reaction mixture. The reaction mixture is cooled to 30° C. and diluted with 220 parts of ethyl acetate. Precipitated sodium chloride is removed by filtration and washed with ethyl acetate. The combined epichlorohydrin solution is washed with 100 parts of a 10% aqueous solution of $NaH_2PO_4$ and with water and dried over $Na_2SO_4$. The epichlorohydrin is removed by distillation in a rotary evaporator and the residue is dried at 140° C./0.02 bar.

Yield: 104 parts (88% of theory)
Softening point: 80° C.
$\overline{M}n$ (gel permeation chromatography in THF)=2489, $\overline{M}w/\overline{M}n$=9.64
Epoxide content: 3.63 eq./kg.

EXAMPLE 2

Polycondensate of 2,2,6,6-tetramethylolcyclohexanol and glyoxal, etherified with epichlorohydrin

Part A: Preparation of the hydroxylated polycycloacetal

In accordance with the procedure of Example 1, Part A, 220 parts of 2,2,6,6-tetramethylolcyclohexanol are suspended in 430 parts of toluene in the presence of 0.7 part of hypophosphorous acid. Then 72 parts of an aqueous solution of glyoxal are added dropwise to this suspension.

Yield: 244 parts (100% of theory)
Softening point: 89°–94° C.
$\overline{M}n$ (gel permeation chromatography in THF)=399, $\overline{M}w/\overline{M}n$=1.148
Hydroxyl content: 17.16 eq./kg.

Part B: Preparation of the epoxidised polycycloacetal

In accordance with the procedure of Example 1, Part B, 140 parts of the polycycloacetal obtained in Part A are dissolved in 100 parts of epichlorohydrin in the presence of 12 parts of a 50% aqueous solution of tetramethylammonium chloride. Then 211 parts of a 50% aqueous solution of sodium hydroxide are added dropwise to the above solution. A yellow oil is obtained.

Yield: 100 parts (48% of theory)
$\overline{M}n$ (gel permeation chromatography in THF)=746, $\overline{M}w/\overline{M}n$=3.095
Epoxide content: 6.11 eq./kg.

EXAMPLE 3

Polycondensate of bis(trimethylol)propane and glutaraldehyde, etherified with epichlorohydrin

Part A: Preparation of the hydroxylated polycycloacetal

In accordance with the procedure of Example 1, Part A, 125 parts of bis(trimethylol)propane (Perstorp AG, Perstorp, Sweden) are suspended in 430 parts of toluene in the presence of 0.5 part of hypophosphorous acid. Then 91 parts of a 50% aqueous solution of glutaraldehyde are added dropwise to the suspension. A highly viscous product is obtained.

Yield: 160 parts (100% of theory)
$\overline{M}n$ (gel permeation chromatography in THF)=2233, $\overline{M}w/\overline{M}n$=2.33
Hydroxyl content: 2.60 eq./kg.

Part B: Preparation of the epoxidised polycycloacetal

In accordance with the procedure of Example 1, Part B, 82 parts of the polycycloacetal obtained in Part A are dissolved in 100 parts of epichlorohydrin in the presence of 0.9 part of a 50% aqueous solution of tetramethylammonium chloride. Then 19 parts of a 50% aqueous solution of sodium hydroxide are added dropwise to the above solution over 5 hours. A yellow oil is obtained.

Yield: 86 parts (90% of theory)
$\overline{M}n$ (gel permeation chromatography in THF)=2949, $\overline{M}w/\overline{M}n$=3.93
Epoxide content: 0.90 eq./kg.

EXAMPLE 4

Polycondensate of bis(trimethylol)propane and glyoxal, etherified with epichlorohydrin

Part A: Preparation of the hydroxylated polycycloacetal

In accordance with the procedure of Example 1, Part A, 500 parts of bis(trimethylol)propane are suspended in 860 parts of toluene in the presence of 2.8 parts of hypophosphorous acid. Then 145 parts of a 40% aqueous solution of glyoxal are added dropwise to this suspension. A highly viscous product is obtained.

Yield: 508 parts (97% of theory)

$\overline{M}n$ (gel permeation chromatography in THF)=652, $\overline{M}w/\overline{M}n$=1.54

Hydroxyl content: 12.28 eq./kg.

Part B: Preparation of the epoxidised polycycloacetal

In accordance with the procedure of Example 1, Part B, 488 parts of the polycycloacetal obtained in Part A are dissolved in 2273 parts of epichlorohydrin in the presence of 16.3 part of a 50% aqueous solution of tetramethylammonium chloride. Then 527 parts of a 50% aqueous solution of sodium hydroxide are added dropwise to the above suspension over 3.5 hours. A brown oil is obtained.

Yield: 582 parts (90% of theory)

$\overline{M}n$ (gel permeation chromatography in THF)=859, $\overline{M}w/\overline{M}n$=2.69

Epoxide content: 5.33 eq./kg.

EXAMPLE 5

Polycondensate of diglycerol and glutaraldehyde, etherified with epichlorohydrin Part A: Preparation of the hydroxylated polycycloacetal In accordance with the procedure of Example 1, Part A, 415 parts of diglycerol (Tokyo Kasei via Ralupur, Zürich) are suspended in 1070 parts of toluene in the presence of 2.3 parts of hypophosphorous acid. Then 333 parts of a 50% aqueous solution of glutaraldehyde are added to the above suspension. A highly viscous product is obtained.

Yield: 374 parts (72% of theory)

$\overline{M}n$ (gel permeation chromatography in THF)=1020, $\overline{M}w/\overline{M}n$=2.15

Hydroxyl content: 6.25 eq./kg.

Part B: Preparation of the epoxidised polycycloacetal

In accordance with the procedure of Example 1, Part B, 366 parts of the polycycloacetal obtained in Part A are dissolved in 1058 parts of epichlorohydrin in the presence of 7.1 parts of a 50% aqueous solution of tetramethylammonium chloride. Then 201 parts of a 50% aqueous solution of sodium hydroxide are added dropwise to the above solution over 3 hours. A yellow oil is obtained.

Yield: 403 parts (90% of theory)

$\overline{M}n$ (gel permeation chromatography in THF)=1798, $\overline{M}w/\overline{M}n$=3.07

Epoxide content: 3.90 eq./kg.

EXAMPLE 6

Polycondensate of bis(trimethylol)propane and glutaraldehyde, etherified with epichlorohydrin Part A: Preparation of the hydroxylated polycycloacetal In accordance with the procedure of Example 1, Part A, 125 parts of bis(trimethylol)propane are suspended in 430 parts of toluene in the presence of 0.5 part of hypophosphorous acid. Then 67 parts of a 50% aqueous solution of glutaraldehyde are added dropwise. A highly viscous product is obtained.

Yield: 138 parts (95% of theory)

$\overline{M}n$ (gel permeation chromatography in THF)=1155, $\overline{M}w/\overline{M}n$=1.76

Hydroxyl content: 5.07 eq./kg.

Part B: Preparation of the epoxidised polycycloacetal

In accordance with the procedure of Example 1, Part B, 100 parts of the polycycloacetal obtained in Part A are dissolved in 235 parts of epichlorohydrin in the presence of 0.9 part of a 50% aqueous solution of tetramethylammonium chloride. Then 45 parts of a 50% aqueous solution of sodium hydroxide are added dropwise to the above solution over 5 hours. A yellow oil is obtained.

Yield: 99 parts (88% of theory)

$\overline{M}n$ (gel permeation chromatography in THF)=1298, $\overline{M}w/\overline{M}n$=1.55

Epoxide content: 2.93 eq./kg.

Use Examples

EXAMPLE I

Preparation of a powder coating composition

Components:
- 145 g of epoxy resin according to Example 1,
- 855 g of a solid, carboxyl-terminated, saturated polyester (URALAC ® 3400, supplied by Scado, acid content: 0.61 eq./kg),
- 20 g of a mixture of 12.5 parts by weight of alkyl trimethylammonium bromide (Morphan ® CHSA, supplied by ABM Chemicals) and 87.5 parts by weight of a solid, saturated, carboxyl-terminated polyester resin (Neoxil ® TPC 83, supplied by Savid).

The components are milled together for 30 seconds in an analytical mill. The resultant powder is then applied to a cleansed aluminium sheet and cured for 30 minutes at 180° C. The colourless finish has a thickness of 40–60 μm and has very good mechanical properties and very good resistance to weathering. The test values are reported in the table.

EXAMPLE II

Preparation of a solvent-containing varnish

Components:
- 90 g of epoxy resin according to Example 2,
- 910 g of a solid, carboxyl-terminated, saturated polyester (URALAC ® 3400, supplied by Scado, acid content: 0.61 eq.kg),
- 20 g of a mixture of 12.5 parts by weight of alkyl trimethylammonium bromide (Morphan ® CHSA, supplied by ABM Chemicals) and 87.5 parts by weight of a solid, saturated, carboxyl-terminated polyester resin (Neoxil ® TPC 83, supplied by Savid).
- 680 g of dimethyl formamide.

The components are dissolved in DMF. The resultant solution is applied to a cleansed aluminium sheet and cured for 30 minutes at 180° C. The colourless finish obtained has a thickness of 50 μm and has very good mechanical properties and very good resistance to weathering. The test values are reported in the table.

TABLE 1

| Test | Example I | Example II |
|---|---|---|
| Erichsen indentation (DIN 53 156, mm) | >10 | >10 |
| impact strength[2] (cm · kg) | >180 | >180 |
| acetone test[2] (rating) | 2–3 | 3 |

TABLE 1-continued

| Test | Example I | Example II |
|---|---|---|
| adhesion[3] (cross-hatch, rating) | 0 | 0 |

[1] A punch of known weight is dropped from a specific height from behind on to the coated aluminium sheet. The value obtained (height × weight) indicates the greatest impact at which the finish still remains intact.
[2] A piece of cloth soaked in acetone is left for 1 minute on the coated surface. The treated surface is then tested for its resistance by scratching with the finger nail. Evaluation is made in accordance with a rating from 0 to 5, with 0 denoting excellent resistance and 5 poor resistance.
[3] Evaluation is made in accordance with a rating from 0 to 5, with 0 denoting excellent adhesion and 5 poor adhesion.

EXAMPLE III

Fabrication of moulded articles 95 parts of the tetraglycidyl ether obtained in Example 6 and 37 parts of hexahydrophthalic anhydride are mixed and the mixture is poured into moulds measuring $150 \times 150 \times 4$ mm$^3$ and cured for 6 hours at 160° C. and for 12 hours at 180° C. The dark yellow, impact-resistant and blemish-free sheets obtained are cut into test specimens, which are then tested for the following mechanical properties:

| | |
|---|---|
| flexural strength (ISO 178): | 94.5 N/mm$^2$ |
| edge elongation (ISO 178): | 4.6% |
| impact strength (ISO 179): | 76.0 kJ/m$^2$ |
| heat deflection temperature (ISO 75): | 51° C. |
| boiling water absorption (1 h at 100° C.): | 0.89% |

EXAMPLES IV AND V

Preparation of solvent-containing varnishes

| Components (g) | IV | V |
|---|---|---|
| epoxy resin of Example 4 | 100 | |
| epoxy resin of Example 5 | | 100 |
| titanium dioxide RN 56 (suppl. by Titangesellschaft) | 266 | 215 |
| isobutyl methyl ketone | 50 | 40 |
| carboxyl-terminated saturated polyester (Degolan ® VP WL 329 DEGUSSA, acid content: 1.47 eq./kg) | 500 | 370 |
| curing accelerator consisting of 25 parts of 4-dimethylaminopyridine, 25 parts of zinc octoate, 25 parts of xylene and 25 parts of butanol | 2 | 2 |

Each of the solutions is applied to a cleansed aluminium sheet and cured for 20 minutes at 200° C. The finishes obtained have a thickness of ca. 40 μm and have the properties indicated in Table 2. The tests are carried out as described in Use Examples I and II.

TABLE 2

| Test | Example IV | Example V |
|---|---|---|
| Erichsen indentation (mm) | 6.8 | 7.6 |
| impact strength (cm · kg) | >90 | >90 |
| acetone test (rating) | 2 | 3 |
| adhesion (cross-hatch, rating) | 0 | 0 |
| bend test 3 m (DIN 53152) | 180 | 180 |

What is claimed is:
1. An epoxidized polycycloacetal of formula I

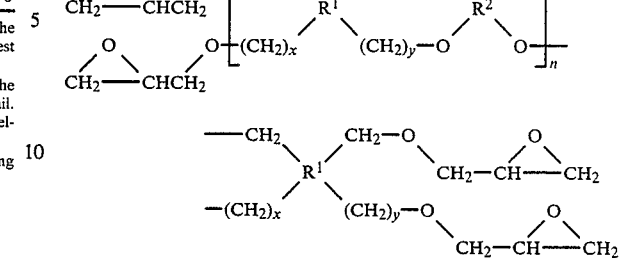

wherein n is as integer from 1 to 500, x and y are each independently of the other 0 or 1, R$^1$ is a carbon atom, a tetravalent hydrocarbon radical having a molecular weight not greater than 1000 or a tetravalent hydrocarbon radical having a molecular weight not greater than 1000 which contains ether oxygen atoms, hydroxyl, carbonyl or epoxy groups, and R$^2$ is a tetravalent hydrocarbon radical derived from a dialdehyde or a diketone.

2. A polycycloacetal according to claim 1, wherein x and y are each 1.

3. A polycycloacetal according to claim 1, wherein one of the symbols x and y is 1 and the other is 0.

4. A polycycloacetal according to claim 1, wherein n is an integer from 1 to 50.

5. A polycycloacetal according to claim 1, wherein R$^1$ is a carbon atom or a tetravalent C$_2$-C$_{24}$aliphatic, C$_5$-C$_{24}$cycloaliphatic or C$_6$-C$_{24}$aromatic radical.

6. A polycycloacetal according to claim 5, wherein R$^1$ is a carbon atom or a tetravalent C$_2$-C$_{12}$aliphatic, C$_5$-C$_{12}$cycloaliphatic radical or a C$_6$-C$_{12}$aromatic radical.

7. A polycycloacetal according to claim 6, wherein R$^1$ is a carbon atom or a group of formula

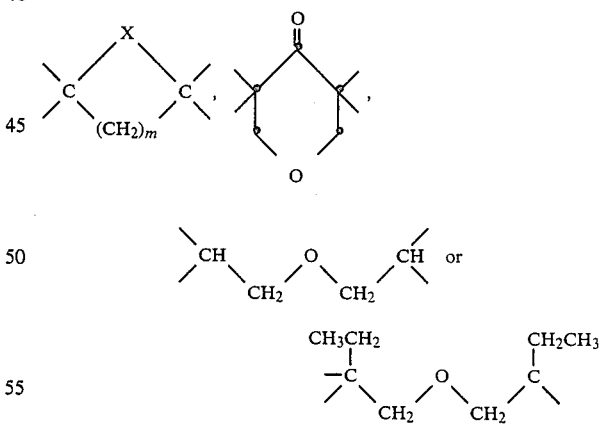

wherein X is a group selected from

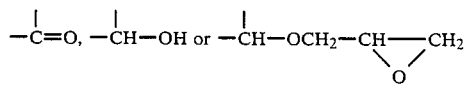

and m is an integer from 2 to 5.

8. A polycycloacetal according to claim 1, wherein R$^2$ is a tetravalent C$_2$-C$_{12}$aliphatic radical, C$_5$-C$_{12}$cycloaliphatic radical or C$_6$-C$_{12}$aromatic radical.

9. A polycycloacetal according to claim 8, wherein $R^2$ is a group of formula

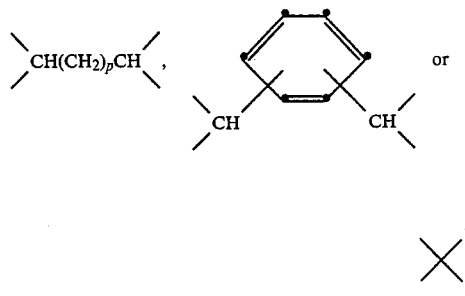 or

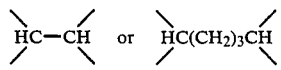

wherein p is 0 or an integer from 1 to 10 and r and s are each independently of the other an integer from 1 to 5 and the sum of r+s is ≦6.

10. A polycycloacetal according to claim 9, wherein $R^2$ is a group of formula

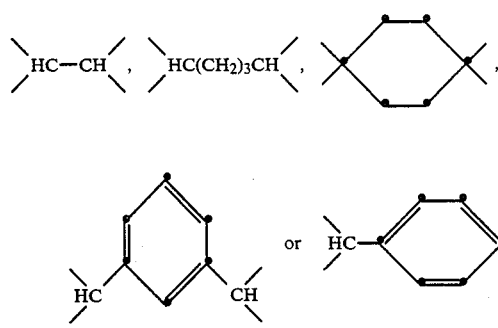

11. A polycycloacetal according to claim 1, wherein $R^2$ is

HC—CH  or  HC(CH₂)₃CH and $R^1$, where x and y are 1, is

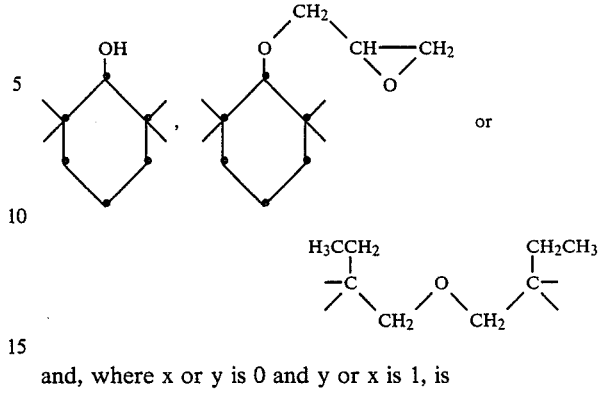

and, where x or y is 0 and y or x is 1, is

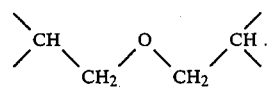

12. A process for the preparation of a polycycloacetal as claimed in claim 1, which comprises reacting a polyol of formula II

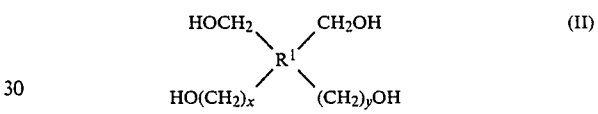

with a dialdehyde or a diketone to give a hydroxylated polycycloacetal of formula III

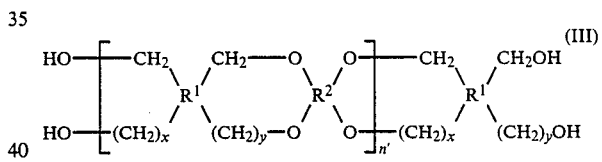

and subsequently glycidylating the compound of formula III with epichlorohydrin, in which formulae (II) and (III) above x, y, $R^1$ and $R^2$ have the meanings given in claim 1 and n' is an integer from 1 to 500.

13. A curable mixture comprising
   (a) an epoxidized polycycloacetal as claimed in claim 1 and
   (b) a hardener therefor.

14. A curable mixture comprising
   (a) an epoxidized polycycloacetal as claimed in claim 1 and
   (b) a hardener and a curing catalyst for epoxy resins.

* * * * *